United States Patent [19]

Kulprathipanja

[11] Patent Number: 4,837,315

[45] Date of Patent: Jun. 6, 1989

[54] PROCESS FOR SEPARATING GLUCOSE AND MANNOSE WITH CA/NH4 - EXCHANGED ION EXCHANGE RESINS

[75] Inventor: Santi Kulprathipanja, Hoffman Estates, Ill.

[73] Assignee: UOP, Des Plaines, Ill.

[21] Appl. No.: 64,642

[22] Filed: Jun. 22, 1987

[51] Int. Cl.[4] ........................ C07H 1/06; C13K 13/00

[52] U.S. Cl. .................................... 536/127; 536/124; 129/46.1; 129/46.2

[58] Field of Search ............... 536/124, 127; 127/46.1, 127/46.2

[56] References Cited

U.S. PATENT DOCUMENTS

| | | | |
|---|---|---|---|
| 4,287,001 | 9/1981 | Kulprathipanja et al. | 536/127 |
| 4,295,994 | 10/1981 | Kulprathipanja | 536/127 |
| 4,298,501 | 11/1981 | Kulprathipanja | 536/127 |
| 4,340,724 | 7/1982 | Neuzil et al. | 536/127 |
| 4,442,285 | 4/1984 | Neuzil et al. | 536/124 |
| 4,444,961 | 4/1984 | Timm | 526/88 |
| 4,471,114 | 9/1984 | Sherman et al. | 536/127 |
| 4,516,566 | 5/1985 | Chao et al. | 127/46.3 |
| 4,581,447 | 4/1986 | Arena | 536/125 |

FOREIGN PATENT DOCUMENTS 1540556 2/1979 United Kingdom .

OTHER PUBLICATIONS

J.A.C.S., vol. 69 (1947), pp. 1963–1965.

Organic Chemistry, Morrison and Boyd (3rd. Ed. 1973), pp. 1078–1079 (Kiliani-Fischer Synthesis).

*Primary Examiner*—Ronald W. Griffin
*Assistant Examiner*—Nancy S. Carson
*Attorney, Agent, or Firm*—Thomas K. McBride; John F. Spears, Jr.; Jack H. Hall

[57] ABSTRACT

Mannose is separated from mixtures with glucose and other saccharides by adsorption of sulfonated polystyrene divinylbenzene crosslinked ion exchange resins, and desorbing the adsorbate with water. Glucose is removed from the adsorption process in the raffinate.

5 Claims, 1 Drawing Sheet

PROCESS FOR SEPARATING GLUCOSE AND MANNOSE WITH CA/NH4 - EXCHANGED ION EXCHANGE RESINS

BACKGROUND OF THE INVENTION

1. Field of the Invention

The field of art to which this invention pertains is the solid bed adsorptive separation of glucose and mannose. The process employs an adsorbent, a sulfonated cross-linked styrene-divinylbenzene resins to selectively adsorb mannose from a mixture of glucose and mannose. The ion exchange resins are used in the form of a calcium-ammonium exchanged ion exchange mixture.

Mannose can be prepared in several ways, but usually the product is mixed with glucose. According to Bilik (Chem. Zvesti, 26, pp 183–6 (1972)), mannose may be epimerized catalytically to glucose in 25% yield. U.S. Pat. No. 4,029,878 discloses a catalytic epimerization process in which greater yields can be obtained. L-mannose is produced, along with L-glucose, from L-arabinose by cyanide addition and hydrogenation, according to Arena et al. U.S. Pat. No. 4,581,447. Using L-aribinose at 95% purity or greater, a mixture of L-glucose and L-mannose is produced in almost a 2:1 ratio with about 1% arabinose as an impurity. L-arabinose is one of the few L-sugars available freely in nature, such as from sugar beet pulp and rice hulls. The L-sugars have become more important in recent years, with the greater attention to caloric intake, due to the potentially non-metabolizing property of some of the L-derivatives, particularly L-sucrose, L-glucose and L-fructose. Thus, L-sugars are potentially commercially as important as D-sugars, and it is intended to refer to both herein. According to U.S. Pat. No. 4,516,566, L-arabinose may be obtained from different sources of cellulose, e.g., beet pulp, wood, along with other saccharides in the product mixtures depending upon the source of cellulose (U.S. Pat. No. 4,516,566 at column 1, lines 53–58). Further, U.S. Pat. No. 4,440,885 discloses two other methods for deriving L-glucose and L-mannose from L-arabinose: The Sowden-Fischer conversion (J.A.C.S. Vol. 69 (1947) pp 1963–65) and the Kiliani-Fischer synthesis (*Organic Chemistry,* Morrison and Boyd (3rd. Ed. 1973) pp 1078–9).

2. Description of the Prior Art

It is known from Sherman et al. U.S. Pat. No. 4,471,114 that mannose and glucose can be separated from a solution of the same by selective adsorption on certain cation-exchanged type X or type Y zeolitic molecular sieves. Specifically, Ba-exchanged X- or Y-type and Sr-, Na- and Ca-exchanged Y-type zeolites will selectively adsorb mannose thereon. The nonadsorbed portion is removed from contact with the zeolite. The mannose can be desorbed from the zeolite with a desorbent and recovered.

It is also known from Brit. Pat. No. 1,540,556 (I.C.I.) to separate mannose from glucose by adsorption with a cationic exchange resin, such as Amberlite XE 200, in calcium form. It has been reported, however, that a two-stage separation, using the identical column in each stage, is required to produce a 98% mannose product. However, good separation can't be obtained in a simple column without reflux. Such a process is inefficient and prohibitively expensive.

SUMMARY OF THE INVENTION

It is accordingly an object of the invention to provide a process for separating mannose from glucose in order to obtain an economical way to obtain mannose in good yield. The industry also desires the L-sugars as substitute sweeteners to satisfy the ultimate food and confections customers' craving for a non-fattening sweetener with little or no physiological side effects. Another object of the invention is to provide a process for separating mannose from a mixture containing glucose and mannose by an adsorption process using a cationic exchange resin exchanged by calcium and ammonium ions. More specifically, the resin used is a partial calcium and partial ammonium salt of a sulfonated polystyrene polymer 4.5 to about 6.5% crosslinked by divinylbenzene.

As hereinbefore set forth, the present invention is concerned with a process for separating mannose from an aqueous mixture containing glucose and mannose. The process is effected by passing a feed mixture containing one or more components over an adsorbent comprising an ion exchange resin exchanged with a mixture of calcium and ammonium ions. The passage of the feed stream over the adsorbent will result in the adsorption of mannose while permitting glucose and the other components of the feed stream to pass through the treatment zone in an unchanged condition. Thereafter, the mannose will be desorbed from the adsorbent by treating the adsorbent with a desorbent material, preferably water. Adsorption and desorption conditions include a temperature in the range of from about 20° to about 200° C. and a pressure in the range of from about atmospheric to about 500 psig to ensure a liquid phase. The preferred conditions are 65° C. and about 50 psig.

DETAILED DESCRIPTION OF THE INVENTION

Figure 1:
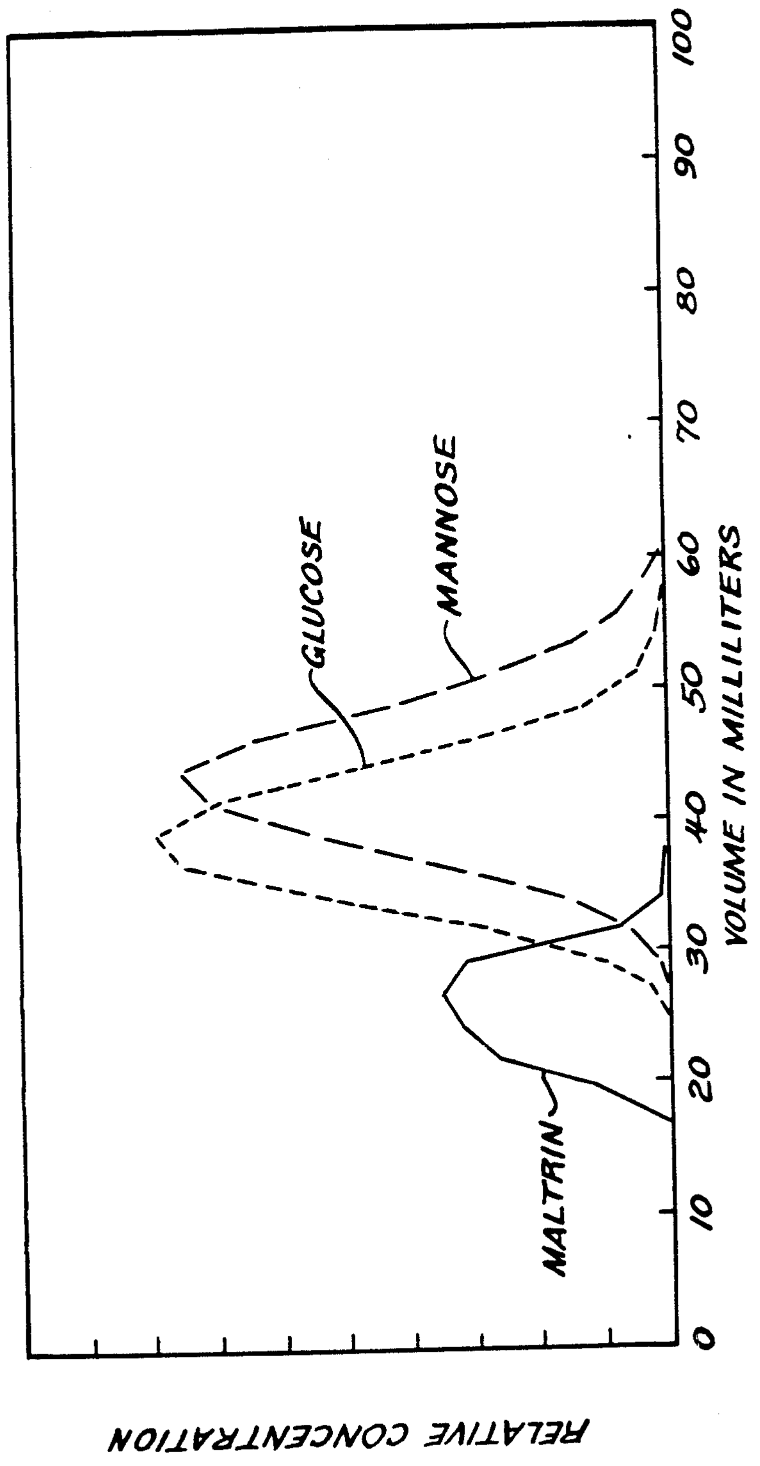
FIG. 1 is a chromatographic trace showing separation of mannose from glucose by an adsorbent, comprising a strong acid cation exchange resin having exchangeable ionic sites exchanged by $Ca^{++}$ and $NH_4^+$ in combination.

For purposes of this invention, the various terms which are hereinafter used may be defined in the following manner.

A "feed mixture" is a mixture containing one or more extract components and one or more raffinate components to be separated by the process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably, at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream.

The feed mixtures which are charged to the process of the present invention will comprise sugar sources, a specific source which is utilized in the present invention comprising mannose epimerization products. As I have found, mannose epimerization products can contain about 65% glucose and 35% mannose.

The adsorbents of the present invention have been found to adsorb mannose selectively over glucose. In addition, it has also been found that the initial performance of the adsorbent is maintained during the actual use in the separation process over an economically desirable life. In addition, as previously set forth, the adsorbent of this invention possesses the ability to separate components of the feed, that is, that the adsorbent possesses adsorptive selectivity for one component as compared to other components. The adsorbents used in the separation of this invention are the ion exchange resins in which the exchange sites are exchanged with a mixture of calcium and ammonium ions. The resins may be made by the process described in U.S. Pat. No. 4,444,961, which provides for very uniform spherical size in the polymeric beads. This patent is hereby incorporated in its entirety by reference. As with other adsorbents, the ion exchange resin preferred in the invention has exchange sites exchanged with ammonium ions for part of the calcium ions the zeolite is initially prepared with. In some cases, the resin may be available in the hydrogen form, and the resin may be exchanged first with calcium and then with ammonium. Alternatively, the resin may be exchanged with both ions in a single solution in a ratio calculated or experimentally determined to exchange the respective ions in the desired ratio. Preferably, the weight ratio based on total weight of resin and ions of calcium exchanged ions to ammonium-exchanged ions is from 2:7 to 3.5:5.5, but the ratio may be from 2:7 to 8:1. Exchange methods are well known to those of ordinary skill in the art and are suitable for the resins of this invention.

The preferred polymerizable monomers are monomers polymerizable using suspension polymerization techniques. Suspension polymerizable monomers are well known in the art and reference is made to *Polymer Processes,* edited by Calvin E. Schildknecht, published in 1956 by Interscience Publishers, Incorporated, New York, Chapter III, "Polymerization in Suspension" by E. Trommsdoff and C. E. Schildkneckt, pp. 69–109 for purposes of illustration. In Table II on pp. 78–81 of Schildknecht are listed diverse kinds of monomers which can be employed in the practice of this invention. Of such suspension polymerizable monomers, of particular interest herein are the water-insoluble monomers including the monovinylidene aromatics such as styrene, vinyl naphthalene, alkyl substituted styrenes (particularly monoalkyl substituted styrenes such as vinyltoluene and ethyl vinylbenzene) and halo-substituted styrenes such a bromo- or chlorostyrene, the polyvinylidene aromatics such as divinylbenzene, divinyltoluene, divinyl xylene, divinyl naphthalene, trivinylbenzene, divinyl diphenyl ether, divinyl diphenyl sulfone and the like; halo olefins, particularly the vinyl halides such as vinyl chloride; esters of alpha, beta-ethyl-enically unsaturated carboxylic acids, particularly acrylic or methacrylic acid, such as methyl methacrylate and ethyl acrylate; vinyl acetate and mixtures of one or more of said monomers. Of said monomers, the monovinylidene aromatics, particularly styrene or a mixture of styrene with a monoalkyl substituted styrene; the polyvinylidene aromatics, particularly divinylbenzene; esters of alpha, beta-ethyl-enically unsaturated carboxylic acid, particularly methyl methacrylate or combinations thereof, particularly a mixture of styrene and divinylbenzene or styrene, divinylbenzene and methyl methacrylate are preferably employed herein.

Also included within the polymerizable monomers useful herein are those monomers which form a solution with a liquid, generally water, wherein the resulting solution is sufficiently insoluble in one or more other liquids, generally a water-immiscible oil or the like, such that the monomer solution forms droplets upon its dispersion in said other liquid. Representative of such monomers are water-soluble monomers which can be polymerized using conventional water-in-oil suspension (i.e., inverse suspension) polymerization techniques such as described by U.S. Pat. No. 2,982,749 which is hereby incorporated by reference, including ethylenically unsaturated carboxamides such as acrylamide, methacrylamide, fumaramide and ethacrylamide; aminoalkyl esters of unsaturated carboxylic acids and anhydrides; ethylenically unsaturated carboxylic acids, e.g., acrylic or methacrylic acid, and the like. Preferred of such monomers for use herein are the ethylenically unsaturated carboxamides, particularly acrylamide, and the ethylenically unsaturated carboxylic acids, particularly acrylic or methacrylic acid. The monomer phase of such water-soluble monomers will generally contain sufficient amounts of water to solubilize the monomer. In such cases, although the amounts of the monomer and water most advantageously employed will vary depending on many factors including the specific polymer and desired end use application, the monomer generally constitutes less than about 90 weight percent of the monomer phase. Preferably, these watersoluble monomers constitute from about 5 to about 80, more preferably from about 30 to about 55, weight percent of the monomer phase.

Relative selectivity can be expressed not only for one feed compound as compared to another but can also be expressed between any feed mixture component and the desorbent material. The selectivity, (B), as used throughout this specification is defined as the ratio of the two components in the adsorbed phase over the ratio of the same two components in the unadsorbed phase at equilibrium conditions. Relative selectivity is shown as Equation 1, below.

$$\text{Selectivity } (B) = \frac{[\text{wt. percent } C/\text{wt. percent } D]_A}{[\text{wt. percent } C/\text{wt. percent } D]_U} \qquad \text{Equation 1}$$

Where C and D are two components of the feed represented in weight percent and the subscripts A and U represent the adsorbed and unadsorbed phase, respectively. The equilibrium conditions are determined when the feed passing over a bed of adsorbent does not change composition, in other words, when there is no net transfer of material occurring between the unadsorbed and adsorbed phases. Where selectivity of two components approaches 1.0, there is no preferential adsorption of one component by the adsorbent with respect to the other; they are both adsorbed (or nonadsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D.

While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used.

An important characteristic of the adsorbent is the rate of exchange of the extract component of the feed mixture material or, in other words, the relative rate of desorption of the extract component. This characteristic relates directly to the amount of desorbent material that must be employed in the process to recover the extract component from the absorbent; faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step.

Resolution is a measure of the degree of separation of a two-component system, and can assist in quantifying the effectiveness of a particular combination of adsorbent, desorbent, conditions, etc. for a particular separation. Resolution for purposes of this application is defined as the distance between the two peak centers divided by the average width of the peaks at ½ the peak height as determined by the pulse tests described hereinafter. The equation for calculating resolution is thus:

$$R = \frac{L_2 - L_1}{\frac{1}{2}(W_1 + W_2)}$$

where $L_1$ and $L_2$ are the distance, in ml, respectively, from a reference point, e.g., zero to the centers of the peaks and $W_1$ and $W_2$ are the widths of the peaks at ½ the heights of the respective peaks. Resolution for effective separation should be at least 0.3 and preferably at least 0.35 up to 1.5 or greater.

Desorbent materials used in various prior art adsorptive separation processes vary depending upon such factors as the type of operation employed. In the swing-bed system, in which the selectively adsorbed feed component is removed from the adsorbent by a purge stream, desorbent selection is not as critical and desorbent material comprising gaseous hydrocarbons such as methane, ethane, etc., or other types of gases such as nitrogen or hydrogen, may be used at elevated temperatures or reduced pressures or both to effectively purge the adsorbed feed component from the adsorbent. However, in adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinbefore discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component or both would complicate or prevent product recovery. Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Since the raffinate and extract products herein are foodstuffs intended for human consumption, desorbent materials should also be nontoxic. Finally, desorbent materials should also be materials which are readily available and, therefore, reasonable in cost.

A dynamic testing apparatus is employed to test various adsorbents with a particular feed mixture and desorbent material to measure the adsorbent characteristics of adsorptive capacity, selectivity, resolution and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities, resolution and other data for various adsorbent systems. The adsorbent is filled to equilibrium with a particular desorbent material by passing the desorbent material through the adsorbent chamber. The preferred desorbent is water, but ethanol, methanol or acetone can also be used. The feed mixture, containing glucose and mannose, diluted in desorbent is injected for a duration of several minutes. Desorbent flow is resumed, and the glucose and mannose are eluted as in a liquid-solid chromatographic operation. The effluent can be analyzed on-stream or, alternatively, effluent samples can be collected periodically and later analyzed separately by analytical equipment and traces of the envelopes of corresponding component peaks developed.

From information derived from the test, adsorbent performance can be rated in terms of void volume, retention volume for an extract or a raffinate component, selectivity for one component with respect to the other, the resolution between the components and the rate of desorption of an extract component by the desorbent. The retention volume of an extract or a raffinate component may be characterized by the distance between the center of the peak envelope of an extract or a raffinate component and the peak envelope of a tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is against the volume of desorbent pumped during this time interval.

The adsorbent may be employed in the form of a dense compact fixed bed which is alternately contacted with the feed mixture and desorbent materials. In the simplest embodiment of the invention, the adsorbent is employed in the form of a single static bed in which case the process is only semicontinuous. In another embodiment, a set of two or more static beds may be employed in fixed-bed contact with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving bed or simulated moving bed countercurrent flow systems, however, have a much greater separation efficiency that fixed adsorbent bed systems and are, therefore, preferred. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589, incorporated by reference herein. In such a system, it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the present process, it is generally necessary that three separate operational zones be present in order for the process to take place, although, in some instances, an optional fourth zone may be used.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream, with respect to fluid flow in zone 1, is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 by shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet streams. The function of the desorbent zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. Separation will typically be by crystallization. The design and operation of crystallization apparatus are well known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200°, with 20° to about 100° C. being more preferred and a pressure range of from about atmospheric to about 500 psig with from about atmospheric to about 250 psig being more preferred to insure liquid phase. Desorption conditions will include the same range of temperatures and pressures as used for adsorption conditions.

The size of the units which can utilize the process of this invention can vary anywhere from those of pilot plant scale (see for example by assignee's U.S. Pat. No. 3,706,812) to those of commercial scale and can range in flow rates from as little as a few cc's an hour up to many thousands of gallons per hour.

Another embodiment of a simulated moving bed flow system suitable for use in the process of the present invention is the cocurrent high efficiency simulated moving bed process disclosed in U.S. Pat. Nos. 4,402,832 and 4,478,721 to Gerhold, incorporated by reference herein in its entirety. This process may be preferred, because of its energy efficiency and lower capital intensity, where products of slightly lower purity are acceptable.

The examples shown below are intended to further illustrate the process of this invention and are not to be construed as unduly limiting the scope and spirit of said process. The examples present test results for various adsorbent and desorbent materials when using the previously described dynamic testing apparatus.

EXAMPLE I

In this example, a test was run using a $Ca/NH_4$ exchanged sulfonated polystyrene divinylbenzene crosslinked cation exchange resin (Dowex 99 from Dow Chemical Co.) to determine the separation of mannose from a mixture representative of that expected from an epimerization product of L-glucose. The ion exchange resin of this example contains 2.6% calcium and 5.5% nitrogen (as $NH_4^+$ ions) (the resin as made was a calcium salt). The adsorbent was packed in an 8.4 mm diameter column having a total volume of 70 cc. The feed mixture consisted of 10 ml of the carbohydrate mixture given in Table 1 containing 12% of solids.

TABLE 1

| | Wt. % |
|---|---|
| Mannose | 5 |
| Glucose | 5 |
| Maltrin 150 (DP3, DP4+) | 2 |
| Water | 88 |
| | 100 |

Maltrin 150 is a commercially available mixture containing 88% saccharides having a degree of polymerization of 4 or more (DP4+), 8.1% maltotriose, having a DP of 3, about 3% maltose and less than 2% glucose.

The experiment began by passing water desorbent through the column at a flow rate of 1.2 cc/min. and a temperature of 65° C. At a convenient time, 10 ml of feed was injected into the column after which flow of desorbent was immediately resumed. FIG. 1 provides a graphical representation of the adsorbent's retention of the sugars in the feed.

A consideration of the average midpoint for each concentration curve reveals separation of mannose from the glucose in the feed mixture. while a substantial portion of the mannose curve does lie within the glucose curve, there is adequate mannose/glucose selectivity as seen by the differences in retention volume (ΔR.V.) shown in Table 2. B (selectivity) mannose/glucose is 1.32, calculated in the manner discussed heretofore. Excellent selectivity of the adsorbent for mannose compared to glucose was found shown by the large R.V. in Table 2.

TABLE 2

| | At Half Width Height | Net Retention Vol. (R.V.) (ml) | Selectivity (B-M/G) | Resolution Factor (0.5) Height |
|---|---|---|---|---|
| Maltrin 150 | 10 | 0 | | 1.54 |
| Glucose | 12.2 | 13.3 | | .34 |
| Mannose | 12.6 | 17.5 | 1.32 | Reference |

Resolution is adequate for the separation as shown by the following calculation:

$$R = \frac{RV2 - RV1}{\frac{1}{2}(W_1 + W_2)} = \frac{17.5 - 13.3}{\frac{1}{2}(12.2 + 12.6)} = \frac{4.2}{12.4} = 0.34$$

What is claimed is:

1. A process for separating mannose from a mixture of glucose and mannose which comprises contacting said mixture at a temperature of from 20° C. to 200° C. and a pressure sufficient to maintain liquid phase, with an adsorbent comprising a partial calcium and partial ammonium salt of a sulfonated polystyrene polymer, crosslinked with divinylbenzene, selectively adsorbing said mannose, removing the nonadsorbed portion of said mixture from contact with said adsorbent, thereby recovering high purity glucose and desorbent and separating said mannose by desorption with a desorbent comprising water at a temperature of from 20° C. to 200° C. and a pressure sufficient to maintain liquid phase.

2. The process of claim 1 wherein said polymer is crosslinked from about 4.5% to about 6.5%.

3. The process of claim 1 wherein said adsorption and desorption conditions include a temperature range of from about 20° to about 100° C. and a pressure range of from about atmospheric to about 250 psig.

4. The process of claim 1 wherein the weight ratio of calcium to ammonium ions is 2:7 to 8:1.

5. A process for separating mannose from a mixture of glucose and mannose which comprises contacting said mixture with an adsorbent comprising a sulfonated polystyrene polymer, crosslinked with divinylbenzene in which the exchangeable ionic sites are exchanged with calcium and ammonium ions, selectively adsorbing said mannose, removing the nonadsorbed portion of said mixture from contact with said adsorbent with a desorbent and thereby recovering high purity glucose and desorbent, and separating said mannose by desorption with a desorbent at a temperature from 20° C. or 200° C. and a pressure sufficient to maintain liquid phase.

* * * * *